United States Patent [19]  [11]  4,430,252
Ryu  [45]  Feb. 7, 1984

[54] PROCESS FOR SYNTHESIZING A MULTICOMPONENT ACIDIC CATALYST COMPOSITION BY AN ORGANIC SOLUTION METHOD

[75] Inventor: Ji-yong Ryu, Ramsey, N.J.

[73] Assignee: Exxon Research & Engineering Co., Florham Park, N.J.

[21] Appl. No.: 448,697

[22] Filed: Dec. 10, 1982

[51] Int. Cl.$^3$ ............... B01J 31/12; B01J 21/02; B01J 27/14
[52] U.S. Cl. ............... 502/162; 502/171
[58] Field of Search ........... 252/432, 435, 437, 431 R, 252/431 P

[56] References Cited

U.S. PATENT DOCUMENTS

| | | | |
|---|---|---|---|
| 3,100,795 | 8/1963 | Frantz et al. | 252/455 R X |
| 3,840,588 | 10/1974 | Pearson | 252/454 X |
| 3,894,075 | 6/1975 | Schoen | 252/431 R X |
| 3,933,888 | 1/1976 | Schloefer | 252/426 X |
| 3,962,189 | 6/1976 | Russin et al. | 252/431 R |
| 3,984,351 | 10/1976 | Rekeu et al. | 252/431 R X |
| 4,105,846 | 8/1978 | Hoff et al. | 252/431 R |
| 4,118,588 | 10/1978 | Fouquet et al. | 560/211 X |
| 4,147,718 | 4/1979 | Gaenzler et al. | 560/211 X R |
| 4,158,621 | 6/1979 | Swift et al. | 208/114 |
| 4,228,036 | 10/1980 | Swift et al. | 252/437 |
| 4,233,184 | 11/1980 | Cull | 252/431 P X |
| 4,275,052 | 6/1981 | Ryu | 252/466 J X |

*Primary Examiner*—William G. Wright
*Attorney, Agent, or Firm*—R. A. Maggio

[57] ABSTRACT

A process for preparing a catalyst composition wherein a Metal Hydrocarboxide I, such as aluminum secbutoxide, a Metal Hydrocarboxide II, such as silicon ethoxide, an acidic phosphorus-oxygen composition, such as phosphoric acid, and water, are reacted in the presence of a liquid organic medium, such as acetone, to form a catalyst precursor composition, which is then calcined to form the catalyst, is disclosed. The catalyst is useful for condensing carboxylic acids or their ester with aldehydes or acetals to synthesize $\alpha$, $\beta$-ethylenically unsaturated acids or esters, such as methylmethacrylate.

27 Claims, No Drawings

PROCESS FOR SYNTHESIZING A MULTICOMPONENT ACIDIC CATALYST COMPOSITION BY AN ORGANIC SOLUTION METHOD

BACKGROUND OF THE INVENTION

The present invention relates to acidic catalyst compositions, their preparation, and use to synthesize, for example α,β-unsaturated carboxylic acids, their functional derivatives, or olefinic oxygen-containing organic compounds.

It is known that olefinic compounds can be synthesized by reacting aldehydes or acetals with organic compounds containing carbonyl groups such as carboxylic acids, esters, aldehydes, and ketones. Such reactions can be illustrated by the following equations:

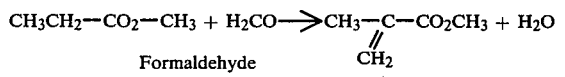

(Eq. 1)

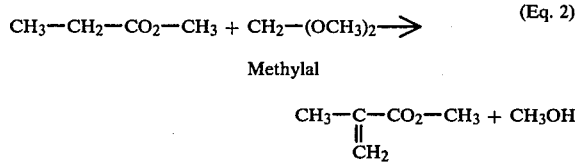

(Eq. 2)

It will be noted that equations 1 and 2 use formaldehyde or methylal, respectively, as alternative reactants. These are conventional reactants which are each associated with certain disadvantages depending on the choice of catalyst. Catalysts employed for the reactions of equations 1 or 2 can broadly be classified as basic or acidic. It is well known, that basic catalysts, when employed in conjunction with reaction of equation 1, will cause disproportionation of formaldehyde to $H_2$, $CO_2$, and methanol, in accordance with the Cannizzaro reaction thereby reducing the selectivity of the reaction to desired products such as methylmethacrylate (MMA) and/or methacrylic acid (MA). In addition, the use of a basic catalyst also causes decarboxylation of the co-reactant carboxylic acid or ester thereof whether formaldehyde is employed as a reactant or not, thereby further reducing the selectivity to desired products. Furthermore when formaldehyde is manufactured in the vapor phase, it is adsorbed and dissolved in water to reduce its potential to polymerize. Methanol is also employed as a polymerization inhibitor. Consequently, formaldehyde is generally sold economically as a 35-45 wt.% mixture of the same with the remainder being water and methanol. The presence of such large amounts of water and methanol makes it difficult to economically achieve a concentrated reactant feed stream. In view of the disadvantages of the base-catalyzed formaldehyde based synthesis route, attempts have been made to replace formaldehyde with a less troublesome reactant such as dimethoxy methane, also known as methylal. However, when methylal is employed in conjunction with a base catalyst, conversion of methylal is very low. Such low conversions are believed to be attributable to the inability of the basic catalyst to efficiently hydrolyze the methylal to formaldehyde which in turn reacts with the carboxylic acid or ester co-reactant. This problem has been alleviated to some extent by the use of acid catalysts. However, even with conventional acid catalysts, the conversion of methylal is still well under 100%. Furthermore, it has been reported (see Albanesi et al discussed hereinafter) that certain acid catalysts also lead to decarboxylation of, for example, methylpropionate producing $CO_2$ and dimethyl ether.

Obviously, the most efficient use of methylal would be to convert 100% thereof to MMA and/or MA while keeping coreactant decarboxylation to a minimum. Such high efficiency reactions are difficult, however, to achieve in practice. A suitable and relatively economic alternative would be to produce reusable by-products which could be recycled in as efficient manner as possible. One reusable by-product from methylal is formaldehyde. However, when less than 100% conversion of methylal occurs, optimum use of process credits would necessitate recovery and recycle not only of formaldehyde, but also of unconverted methylal. This complicates the recycle procedure relative to the recycle of formaldehyde alone. Furthermore, if one seeks to recycle formaldehyde, the decomposition thereof to CO, and $H_2$ must also be minimized. Similar considerations apply to the undesired decarboxylation reactions which also produce unusable products that cannot be recycled.

Accordingly, and in view of the above it would be of extreme economic significance if a catalyst could be developed which is capable of employing either methylal or formaldehyde as a reactant for the production of α,β-ethylenically unsaturated products for carboxylic acids or their derivatives without, or with at least reduced, attendant undesirable side reactions which occur when employing conventional acidic or basic catalysts.

Various processes and catalysts have been proposed for the aforedescribed reactions.

For example, U.S. Pat. No. 3,100,795 describes the use of basic catalysts such as natural or synthetic (e.g. zeolites), alkali and alkaline earth metal aluminosilicates, as well as alkali and alkaline earth metal hyroxides supported on natural or synthetic aluminosilicates or silica gels, to catalyze the reaction between methanol, propionate acid, and formaldehyde to form methylmethacrylate. The conversion to methylmethacrylate based on formaldehyde is reported in Example 5 as 66% and the yield is reported as 99%, although such terms as conversion and yield are left undefined in this patent. Neither the catalysts of the present invention nor the method of its preparation are disclosed in this patent.

U.S. Pat. No. 3,840,588, assigned to Monsanto, describes the use of alkali metal hydroxides or oxides dispersed on a support having a surface area of 350 to 1000 $m^2$/gm. Suitable support materials include aluminas, thorias, magnesias, silica-aluminas, and silicates. In addition to hydroxides or oxides, other alkali metal compounds may be deposited on the support such as carbonates, nitrates, sulphates, phosphates, inorganic salts, acetates, propionates or other carboxylates. All of such supported catalysts are basic catalysts and no reaction between the catalysts and their supports is even alleged, simple impregnation procedures being employed for deposition. These catalysts are employed in the reaction of formaldehyde and saturated alkyl carboxylates to form α,β-ethylenically unsaturated esters at temperatures of at least 400° to 600° C. A methylmethacrylate selectivity of 82 mole % at formaldehyde conversions of 98% are reported in this patent at a reaction temperature of 400° C. and a space time yield of 490 L/hr (Table II, Run 7). However, at 430° C. and higher space time yields of 960 L/hr (Example 1) the selectivity to methylmethacrylate of 92 mole % is obtained at a formaldehyde conversion of only 67%. At reaction temperatures below 400° C., it is alleged that selectivities drop significantly, e.g., to below 40% (see FIG. 2) due to the Cannizzaro reaction (Col. 3, Lines 29 et seq). Moreover, water must be employed in the feed stream in strictly controlled amounts to obtain good selectivity. In the absence of water, formaldehyde conversion is negligible, and in the presence of too much water selectivity drops drastically. The required use of water necessitates the use of alcohols in the feed stream to suppress hydrolysis of the ester reactant and reduce the amount of ester in the reaction zone by acting as a diluent (see Col. 3, Lines 55 et seq) as well as complicating the overall process to implement strict control of the water content of the feed stream. This control of water content can be further complicated by the in-situ production of water in the reactor. Thus, selectivities and yields achieved in this patent are obtained at the sacrifice of simplicity of process design and overall process economics.

U.S. Pat. No. 3,933,888, assigned to Rohm and Haas Co., discloses the reaction of formaldehyde with an alkanoic acid or its ester in the presence of basic catalysts containing basic pyrogenic silica (e.g. SA of 150 to 300 $m^2/g$) alone or impregnated with activating agents which provide additional basic sites to the pyrogenic silica when calcined. Such activating agents include alkali and alkaline earth metal hydroxides, oxides, amides, and salts such as carbonates, oxalates phosphates, e.g., $Na_3PO_4$, $Na_2HPO_4$, $KOCH_3$, $Na_4SiO_4$. The identity, impregnation, and calcination procedures, of the activating agent is always selected to provide a basic catalyst. A molar ratio of alkanoic acid:formaldehyde:-water:methanol of from 1:1:0.01 to 1:1.6:0.03 is disclosed. With a molar ratio of propionic acid:formaldehyde:water:methanol of 20:20:50:1 and a maximum of 34% conversion of formaldehyde and propionic acid to methacrylic acid and methylmethacrylate, selectivities (referred to in this patent as yields) to MA+MMA no greater than 69%, based on formaldehyde converted, or 80%, based on propionic acid converted, are achieved. When reacting methyl propionate with formaldehyde, water and methanol in the same molar ratio, the selectivity to MA+MMA based on a formaldehyde conversion of 25% is 63% (see Ex. 24). Furthermore, from the data of Table III in this patent, it can be calculated that for every 100 moles of formaldehyde in the feed, 34 moles thereof are converted to MA+MMA, and 45 moles thereof remain unreacted. About 21 moles of formaldehyde are unaccounted for.

U.S. Pat. No. 4,118,588, assigned to BASF, is directed to a process for synthesizing $\alpha,\beta$-ethylenically unsaturated acids or esters such as methacrylic acid and methylmethacrylate from the reaction of propionic acid and/or methylpropionate with dimethoxymethane (methylal) in the presence of catalysts (most of which are acidic) based on one or more salts selected from phosphates and silicates of: magnesium, calcium, aluminum, zirconium, thorium and titanium. Such salts can be used alone or together with oxides of the same aforedescribed magnesium et al metals, and additionally boric acid and/or urea. Thus, a typical acidic catalyst consists of aluminum phosphate, titanium dioxide, boric acid, and urea. Included within the list of 62 possible combinations of various materials are aluminum phosphate and aluminum silicate, or aluminum phosphate, aluminum silicate, and boric acid. Such catalysts can be modified with alkali and/or alkaline earth metal: carboxylates, oxides, silicates and hydroxides. The method of catalyst preparation includes mixing and heating the constituent components of the catalyst in water, evaporating the water and drying. Other methods are disclosed, such as forming a paste, or precipitation from an aqueous solution, but each of these alternate methods employs water as the liquid medium. The components of the catalyst are described at Col. 6, Lines 44 et seq, as being present in the catalyst as a mere mixture, as members of a crystal lattice, or in the form of mixed crystals. This patent therefore does not disclose a catalyst composition of the present invention wherein the components thereof have been reacted in a liquid organic medium to form an amorphous or substantially amorphous material, nor does it disclose the method of preparing such a catalyst. The highest conversion of methylal reported in this patent is 92% at a selectivity (referred to in the patent as yield) to MMA of 95% when employing catalyst of $TiO_2$, $AlPO_4$, $H_2BO_4$, and urea, and a reaction time of 30 min. As described hereinafter at Comparative Example 1, such selectivities drop drastically when the reaction time is extended to 2.5 hours after discarding the first 15 minutes of product.

U.S. Pat. No. 4,147,718, assigned to Rohm GmbH, is directed to a method for making $\alpha,\beta$-unsaturated carboxylic acids and their functional derivatives, such as methacrylic acid and methylmethacrylate, from the reaction of methylal (dimethoxymethane) with propionic acid or its corresponding ester or nitrile, in the presence of a catalyst, which catalyst is a combination of silicon dioxide provided with basic sites (as described in U.S. Pat. No. 3,933,888) and aluminum oxide, which optionally may also be provided with basic sites in a similar manner. Aqueous impregnation procedures are employed for incorporation of the basic sites, and the resulting basic silicon dioxide and aluminum oxide components are merely then optionally mixed or arranged in separate layers. Thus, the acid catalysts of the present invention are not disclosed in this patent. The highest selectivity to MMA is 87.1% but at a conversion of propionic acid or methylpropionate of only 13.3%. The highest conversion reported is 42% at a MMA selectivity of 78%.

U.S. Pat. No. 4,324,908, assigned to SOHIO, is directed to a promoted phosphate catalyst for use in synthesizing $\alpha,\beta$-unsaturated productss, which catalyst requires the presence of at least one or more of Fe, Ni, Co, Mn, Cu, or Ag, as promoters in conjunction with phosphorus and oxygen. The catalysts of the present invention do not require the presence of such promoter metals in any form. The highest per pass conversion of methylal to MMA+MA is 52.9% at a methylal conversion of 97.6%.

Albanesi, G., and Moggi, P., Chem. Ind. (Milan) Vol. 63, p. 572-4 (1981) disclose the use of Groups 3, 4, and 5 metal oxides in unsupported, or $SiO_2$ supported form, for the condensation reaction between the methyl hemiacetal or formaldehyde ($CH_3OCH_2OH$) and methylpropionate to form methylmethacrylates. Ten percent $WO_3$ supported on $SiO_2$ is reported as the best catalyst relative to other disclosed catalysts because the decomposition of formaldehyde to CO and $CO_2$ and the decarboxylation of methylpropionate, occur least over this catalyst. However, the highest reported formaldehyde conversion when employing the tungsten catalyst is only 37.5%. Furthermore, it is disclosed that gammaalumina, silica-alumina and molecular sieves tend to convert the hemiacetal of formaldehyde to dimethylether and formaldehyde which in turn tend to immediately decompose to CO and $H_2$ above 400° C. while in contact with these materials.

U.S. Pat. No. 4,275,052, by the inventor herein, is directed to a process for synthesizing a high surface area alumina support (e.g., 300 to 700 m²/g) from organic solutions of aluminum alkoxides by the hydrolysis of these alkoxides with water. In accordance with this process, a first solution of an aluminum alkoxide dissolved in an organic solvent selected from ethers, ketones, and aldehydes, is mixed with a second solution comprising water and a similar organic solvent. The resulting material is dried and calcined, preferably in a water free environment, i.e., a dry gas, since the presence of water at these steps of the preparation will adversely affect the surface area of the alumina. The resulting alumina is used as a support or carrier material for catalytic components capable of promoting various hydrocarbon conversion reactions such as dehydrogenation, hydrocracking, and hydrocarbon oxidations. Conventional promoters are employed for such reactions including platinum, rhenium, germanium, cobalt, palladium, rhodium, ruthenium, osmium and iridium. Thus, the use of these aluminas to catalyze the synthesis of α,β-unsaturated products is not disclosed. Furthermore, the reaction between aluminum alkoxide with other hydrocarboxides, such as a silicon alkoxide, and an acidic phosphorus compound is also not disclosed.

U.S. Pat. No. 4,233,184 is directed to an aluminum phosphate alumina composition prepared by mixing and reacting in the presence of moist air, an aluminum alkoxide and an organic phosphate of the formula $(RO)_3PO$ wherein R is, for example, alkyl or aryl. The phosphorus of the resulting composition is alleged to be in the form of $AlPO_4$ based on x-ray analysis, but in some preparations the amorphous nature of the product is said to make identification of the phosphorus species difficult. The amorphous nature of these samples is believed to be attributable to low calcination temperatures, e.g., below 600° C. The mole ratio of alumina to aluminum phosphate will depend upon the mole ratio of aluminum alkoxide to organic phosphate employed in the synthesis and the amount of aluminum phosphate in the final product can range from 10 to 90% by weight. Mixed alumina-metal oxide-aluminum phosphates are also disclosed wherein a mixture of metal alkoxides can be employed. Thus, a $SiO_2$-$Al_2O_3$-$AlPO_4$ can be prepared from a mixture of silicon alkoxide and aluminum alkoxide with an organic phosphate. However, from the description provided in this patent, it does not appear that the optional metal oxides (e.g. $SiO_2$) added initially as metal alkoxides (e.g. silicon alkoxide) react with the organic phosphate. For example, silicon alkoxide is merely converted to the corresponding oxide, i.e., $SiO_2$. This is confirmed at Col. 3, Lines 3, 18, and 22, and Examples 4 to 9 wherein the optional additional metals are reported as being present as $WO_3$ (Examples 4 and 5) $MoO_3$ (Example 6), $SiO_2$ (Examples 7 and 8), $ZrO_2$ (Example 9) (see also the characterization of Catalyst G, Table VI). The organic phosphates employed in preparing the catalysts of this patent do not possess an acidic hydrogen nor is an ether, aldehyde, or ketone or mixtures thereof employed as a solvent medium (note Example 5 of this patent employs an isopropyl alcohol organic phosphate mixture during the preparation procedure, alcohol alone being impermissible in the present invention) as required by the present invention. The resulting composition is employed as a catalyst or catalyst support for processes such as cracking, hydrocracking, isomerization, polymerization, disproportionation, demetallization, hydrosulfurization, and desulfurization. Use of the composition as a catalyst for the synthesis of α,β-unsaturated products is not disclosed.

Alumina-aluminum phosphate-silica zeolite catalysts are disclosed in U.S. Pat. Nos. 4,158,621 and 4,228,036.

In view of the commercial importance rof α,β-unsaturated produucts, such as methylmethacrylate, there has been a continuing search for catalysts which can produce such products at improved conversions, selectivities, and/or yields. The present invention is a result of this search.

SUMMARY OF THE INVENTION

In one aspect of the present invention there is provided a process for preparing a catalyst composition which comprises: (1) reacting in admixture at least one Metal Hydrocarboxide I, at least one Metal Hydrocarboxide II, at least one acidic phosphorus-oxygen containing compound, and water in the presence of at least one liquid organic medium comprising at least 50% by weight, based on the weight of said medium, of at least one member selected from the group consisting of organic aldehyde, organic ketone, and organic ether, said reaction being conducted in a manner sufficient to (a) avoid contact of Metal Hydrocarboxides I and II with water prior to contact of Metal Hydrocarboxides I and II with the acidic phosphorus-oxygen containing compound and (b) form a catalyst precursor composition; (2) separating said catalyst precursor composition from said reaction admixture; (3) calcining said catalyst precursor composition to form said catalyst composition; wherein said process: (i) the metal $M^1$ of said Metal Hydrocarboxide I is selected from at least one member of the group consisting of Al, Ga, In, and Tl; and (ii) the metal, $M^2$, of said Metal Hydrocarboxide II is selected from at least one member of the group consisting of Si, Sn, and Ge.

In another aspect of the present invention there is provided a catalyst composition prepared by the above process.

In a further aspect of the present invention there is provided a process for using said catalyst composition to prepare α,β-ethylenically unsaturated acids or their acid derivatives.

DESCRIPTION OF PREFERRED EMBODIMENTS

The catalyst composition of the present invention is prepared by reacting at least one Metal ($M^1$) Hydrocarboxide (referred to herein as Hydrocarboxide I), at least one Metal ($M^2$) Hydrocarboxide (referred to herein as Hydrocarboxide II), at least one acidic phosphorus-oxygen containing compound, and water in the presence of at least one liquid organic medium under conditions and in a manner sufficient to form a catalyst precursor composition which is then calcined to form an acidic catalyst composition. The resulting catalyst composition comprises an inorganic amorphous or substantially amorphous oxide material comprising the following components reacted therein:

$$M^1/M^2/P/O \tag{I}$$

wherein $M^1$ is at least one Group 3b element (of the Periodic Chart) selected from Al, Ga, In, and Tl, preferably aluminum, $M^2$ is at least one Group 4b element selected from Si, Sn, and Ge, preferably Si. For ease of discussion and description the aforedescribed Group 3b and 4b elements constituting $M^1$ and $M^2$ are referred to generically as metals, although it is recognized that the term "metal" as applied to Si is an unconventional use of this term.

It is to be understood that the precise structure of the metal-phosphorus oxide catalysts of the present invention has not yet been determined although the components of the catalyst composition are believed to be reacted with each other during the preparative procedure and the resulting catalyst is therefore not believed to be a mere mixture of oxides.

Hydrocarboxides I and II are selected to be capable of undergoing hydrolysis of the organic portion thereof in the presence of water, and capable of being solubilized or at least partially solubilized in the organic medium and other components of the reaction mixture.

Suitable Hydrocarboxides I which can be employed as the starting material can be represented by the structural formula:

$$(M^1)(OR)_3 \qquad (II)$$

wherein $M^1$ is as described above, preferably Al, and R is a substituted or unsubstituted hydrocarbyl radical independently selected from the group consisting of alkyl, typically alkyl having from about 1 to about 8 carbons, preferably from about 2 to about 6 carbons, and most preferably from about 3 to about 4 carbons, aryl, typically aryl having from 6 to about 14 carbons, preferably from about 6 to about 10 carbons, and most preferably 6 carbons, aralkyl, and alkaryl, typically aralkyl and alkaryl wherein the alkyl and aryl portions thereof are as defined immediately above respectively; cycloalkyl, typically cycloalkyl having from about 4 to about 12 carbons, preferably from about 5 to about 10 carbons, and most preferably from about 6 to about 8 carbons, all of the above described hydrocarbyl carbon numbers being exclusive of substituents; said R substituents being selected from ether groups, typically ether groups represented by the structural formulae: $-O-R_1$, $-R_1-O-R_2$, wherein $R_1$ and $R_2$ are independently selected from the group consisting of alkyl, typically about $C_1$ to about $C_{10}$ alkyl, preferably about $C_1$ to about $C_5$ alkyl, and most preferably about $C_1$ to about $C_3$ alkyl; and ester groups, typically ester groups represented by the structural formulae:

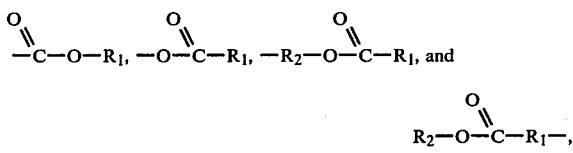

wherein $R_1$ and $R_2$ are as defined above.

Preferred Hydrocarboxide I compounds include the alkoxides.

Representative examples of suitable Hydrocarboxides I of formula II include: aluminum tri: n-butoxide, sec-butoxide, isobutoxide, isopropoxide, n-propoxide, ethoxide, methoxide, phenoxide, benzoxide, nepthoxide, methoxyethoxide, 3-(methoxy carbonyl) propoxide, 3-(ethyl carbonyl oxy) butoxide, cyclohexoxide, 1,3-(dimethyl)-2-phenoxide, 1,2-(methoxy)-4-benzoxide, and mixtures thereof.

Similar representative hydrocarboxides can be formed replacing part, or all of the aluminum present therein with any one or more of the other aforedescribed Group 3b elements.

The preferred Hydrocarboxides I include aluminum: sec-butoxide, n-butoxide, n-propoxide, isopropoxide, methoxide, ethoxide; and mixtures thereof.

Hydrocarboxide II which is employed as a starting material in the precursor forming reaction can be represented by the structural formula:

$$(M^2)(OR)_4 \qquad (III)$$

wherein $M^2$ and R are as described above in connection with structural formulae I and II above, respectively. The specific hydrocarboxide R groups can be the same as illustrated above in connection with the aluminum hydrocarboxides and can be employed with any of the aforedescribed Group 4b elements.

Preferred Hydrocarboxides II include silicon: tetraethoxide, tetra-n-propoxide, tetraisopropoxide, tetramethoxide, tetra-n-butoxide, tetraisobutoxide, and mixtures thereof.

The acidic phosphorus-oxygen containing compound which can be employed as a starting material must possess at least one acidic hydrogen and be capable of reacting with the Hydrocarboxides I and II or the hydrolyzed inorganic product thereof, and the use of the term "acidic phosphorus oxygen compound" is indicative of this requirement. Representative examples of suitable acidic phosphorus-oxygen containing compounds include phosphorus acid ($P(OH)_3$), phosphonous acid ($HP(OH)_2$), phosphinous acid ($H_2POH$), phosphenous acid ($O=POH$), phosphoric acid ($P(O)(OH)_3$), phosphonic acid ($HP(O)(OH)_2$), phosphinic acid ($H_2P(O)(OH)$), phosphenic acid ($O=P(O)OH$), phosphine oxide ($H_3PO$), phosphoranoic acid ($H_4POH$), phosphorane dioic acid ($H_3P(OH)_2$), phosphorane trioic acid ($H_2P(OH)_3$), phosphoranetetroic acid ($HP(OH)_4$), phosphorane pentoic acid ($(P)(OH)_5$), as well as any of the aforenoted acids having one or more but not all of the acidic hydrogens replaced with an alkyl group, typically $C_1$ to $C_{10}$, preferably $C_1$ to $C_5$ and most preferably $C_1$ to $C_3$ alkyl.

In addition, polyphosphoric acid, an acid commerically available as a mixture of orthophosphoric acid with pryophosphoric, triphosphoric and higher acids, sold on the basis of its calculated $H_3PO_4$ content (e.g. 115%), and super phosphoric acid sold at 105% $H_3PO_4$ content, can also be employed as starting materials.

The preferred acidic phosphorus-oxygen compound is phosphoric acid.

Upon hydrolysis of Hydrocarboxides I and II and reaction with the acidic phosphorus oxygen compound, organic alcohols are formed. Since it is desired that residual organic material in the catalyst composition be minimized, it is preferred as a matter of convenience to select the identity of the organic moiety of the Hydrocarboxides such that the alcohols derived therefrom can be easily vaporized, e.g., alkoxides having fewer than about 10 carbons are most preferred.

The organic medium used in the preparation of the catalyst precursor should be a liquid at reaction temperature and is selected from: aldehydes, ketones, ethers, and mixtures thereof typically containing from about 1 to about 20, preferably from about 1 to 10, and most preferably from about 1 to 5 carbon atoms.

More specifically, the organic moiety to which the aldehyde, ketone, and ether functional groups can be attached includes alkyl, typically about $C_1$ to $C_{20}$, preferably about $C_1$ to $C_{10}$, most preferably about $C_1$ to $C_5$ alkyl, aryl, typically about $C_6$ to $C_{14}$, preferably about $C_6$ to $C_{10}$, most preferably $C_6$ aryl, cycloalkyl, typically about $C_4$ to $C_{20}$, preferably about $C_6$ to $C_{12}$, most preferably about $C_6$ to $C_{10}$ cycloalkyl, aralkyl and alkaryl wherein the alkyl and aryl groups thereof are described above.

Each class of liquid organic medium can contain one or more, typically 1 to 3, functional groups as well as mixtures of functional groups. Furthermore, the preferred organic moiety of liquid organic medium is a saturated aliphatic compound.

Representative aldehydes include benzaldehyde, acetaldehyde, propionaldehyde m-tolualdehyde, trioxane, valeraldehyde, butyraldehyde, oxalaldehyde, malonaldehyde, adipaldehyde.

Representative ketones include acetone, 3-pentanone, methylethylketone, cyclohexanone, dimethyl ketone, diethyl ketone, dibutyl ketone, methyl isopropyl ketone, methyl sec-butyl ketone, benzophenone, and mixtures thereof.

Representative ethers include dimethyl ether, diethyl ether, dibutyl ether, tetrahydrofuran, anisole, dioctyl ether, 1,2-dimethoxyethane, 1,4-dimethoxybutane, diethylene ether, 1,1,3,3-tetramethoxypropane, and mixtures thereof.

Preferred organic media comprise acetone, diethylether, acetaldehyde, methylethyl ketone, 3-pentanone, 1,2-dimethoxyethane and mixtures thereof.

The most preferred organic medium is acetone or a mixture of acetone and diethylether.

The organic medium is believed to undergo electrostatic field interactions with the metals of Hydrocarboxides I and II and the reaction intermediates which form upon contact of the Hydrocarboxides I and II, the acidic phosphorus compound and water in the reaction mixture. This interaction is believed to occur through complexation of the organic medium with the various species present in the reaction mixture. Thus, the organic medium is not inert and only certain organic media have been found suitable for this purpose as described herein. The organic medium also functions as a solvent and/or suspending agent for the Hydrocarboxides I and II and phosphorus containing compound, and any complexes and reaction intermediates thereof, as a solvent and/or suspending agent of the resulting catalyst precursor, as a liquid for providing uniform heating and/or mixing of the catalyst forming reactants, and as a medium capable of bringing Hydrocarboxides I and II, the phosphorus-oxygen compound, and water into intimate contact for reaction. To perform the latter function it is desirable to select the organic medium such that it is at least miscible, preferable soluble, with or in, water, the catalyst forming reactants, and the Hydrocarboxide derived alcohol. It is also preferred to select the organic medium so that it will be completely or substantially removed from the catalyst precursor during drying and/or calcination. Thus, organic media with low molecular weight, and high vapor pressure are preferred. Minor amounts of alcohol, such as the hydrocarboxide derived alcohol can be tolerated within the organic medium initially or as it forms. Minor amounts of esters can also be included although this is not preferred. By minor amount as used herein is meant less than 50%, preferably less than 25%, and most preferably less than 10%, by weight of the organic medium. Minor amounts of inert diluents can be employed to reduce the cost of organic medium, such as paraffins, aromatic compounds, and mixtures thereof, although this is not preferred.

Thus, the organic medium is selected so that it is a liquid at reaction temperature, preferably dissolves, or at least partially dissolves the precursor forming reactants and comprises at least 50%, preferably at least 75%, and most preferably at least 90% (e.g. 100%), by weight thereof, of any one or more of said aldehyde ketone, and ether. It is preferred to exclude the presence of any organic alcohol, ester, or acid from the initial starting composition of the liquid organic medium.

The catalyst precursor forming reaction is conducted by providing a reaction admixture comprising at least one Hydrocarboxide I, at least one Hydrocarboxide II, water, and liquid organic medium. However, the order of addition of the components is critical to the extent that it must be conducted in a manner sufficient to avoid contact of either of the Hydrocarboxides I and II with water prior to contact of said Hydrocarboxides I and II with the acidic phosphorus-oxygen containing compound, to avoid premature reaction of the water and the Hydrocarboxides I and II. Thus, a wide variety of admixture sequences are possible subject to the above constraints.

The preferred method of admixture is to initially prepare two separate solutions typically at ambient temperature and pressure. The first solution contains Hydrocarboxides I and II dissolved in a suitable organic liquid medium. The second solution contains the acidic phosphorus-oxygen compound, water, and organic liquid medium, preferably the same medium used in, or at least miscible with, the first solution. The two solutions are then mixed preferably by the addition of solution 2 to solution 1. While very small amounts of water may be tolerated in the first solution, it is preferred that it be anhydrous. An alternative preferred variation is to withhold a portion of the needed amount of Hydrocarboxides I and/or II from the first solution (e.g. withhold about 30% by weight of the total Hydrocarboxide I and/or II, combine the solutions and then add the remainder of Hydrocarboxide I and/or II. Stepwise addition of the Hydrocarboxides can also be accompanied with stepwise addition of organic medium. An alternative addition procedure is to prepare 3 separate solutions containing respectively. Hydrocarboxide I and liquid organic medium (Solution 1), Hydrocarboxide II and liquid organic medium (Solution 2), and the acidic phosphorus-oxygen compound, water, and liquid organic medium (Solution 3). The solutions are then combined simultaneously, or individually by separately adding Solution 3 to Solutions 1 and/or 2, and admixing the resulting solutions.

The relative amounts of Hydrocarboxides I and II and acidic phosphorus-oxygen containing compound employed to form the catalyst precursor forming admixture determines the gram atom ratios of the components in the catalyst. Thus, while any effective amount of said materials may be initially present in said admixture, it is contemplated that such effective amounts constitute a mole ratio of Hydrocarboxide I:Hydroocarboxide II of typically from about 1:3.5 to about 1:0.5, preferably from about 1:2 to about 1:0.7, and most preferably from about 1:1.5 to about 1:0.8. The mole ratio of Hydrocarboxide I:acidic phosphorus-oxygen compound in the reaction mixture is typically controlled to be from about 1:1.5 to about 1:0.5, preferably from about 1:1.25 to about 1:0.7, and most preferably from about 1:1.1 to about 1:0.85.

Water is also critical to the catalyst preparative process of the present invention. The water hydroxyzes Hydrocarboxides I and II to form alcohols and corresponding metal oxides and/or hydroxides. Consequently, the amount of water employed is related to the amount of Hydrocarboxides I and II present in the reaction admixture and preferably is effective to obtain complete hydrolysis thereof. Exact stoichiometric ratios, however, are not required. Thus, while any effective amount of water can be employed to form the reaction admixture, it is contemplated that such effective amounts constitute a mole ratio of the sum of the moles of Hydrocarboxides I and II: $H_2O$ of typically from about 3:1 to about 1:300, preferably from about 2:1 to about 1:10, and most preferably from about 1:1 to about 1:6.

The precursor forming reaction must be conducted in the presence of at least some liquid organic medium (the composition of which is defined above). As the amount of suitable ether, aldehyde, and/or ketone liquid organic medium employed in the reaction mixture is decreased, the concentration of the Hydrocarboxide derived alcohol produced in-situ increases to the extent that the aforedescribed complexation is decreased and the undesirable effects associated with employing alcohol as the predominant organic medium during the precursor formation become increasingly more pronounced, namely, the yield of the $\alpha$, $\beta$-unsaturated products described herein suffers drastically. The amount of organic medium present during the precursor forming reaction is therefore selected to effect a stirrable solution or partial solution of reactants, and improve the yield of $\alpha$, $\beta$-unsaturated product derived from the use of the resulting catalyst relative to the yield of said product obtainable from a catalyst prepared in the absence of said organic medium. Thus, while any effective amount of organic medium may be employed, it is contemplated that such effective amount constitute typically at least about 25%, preferably at least about 40%, and most preferably at least about 50%, and can range typically from about 25 to about 95%, preferably from about 40 to about 90%, and most preferably from about 60 to about 85%, by weight, of the reaction admixture, based on the combined weight of Hydrocarboxides I and II, and phosphorus-oxygen compound, organic medium and water.

Furthermore, it is contemplated that the amount of water in the reaction mixture is controlled to be typically not greater than about 25%, preferably not greater than about 20%, and most preferably not greater than about 15%, and will vary typically from about 5 to about 25%, preferably from about 8 to about 20%, and most preferably from about 10 to about 15%, by weight, based on the combined weight of liquid organic medium and water in the precursor forming admixture.

The resulting admixture is preferably mixed vigorously and continuously during its formation and during the reaction to effect intimate contact and reaction between the component reactants of the admixture. This can be achieved with conventional stirring means, by refluxing or both. Thus, in a batch operation an especially convenient means of conducting the admixing is to mechanically stir one solution while admixing into it the other solution. In a continuous mixing operation a convenient means of conducting the admixing is to simultaneously pump the two solutions through a single means such as an in-line mixer. If reluxing is employed during the catalyst precursor forming reaction, the liquid organic medium is preferably selected so that it will boil at the selected reaction temperature described hereinbelow. Removal of the Hydrocarboxides I and II derived alcohol by-product by distillation can also be employed and is preferred when large amounts of said alcohol by-product are produced in-situ.

The precursor forming reaction temperature is effective to achieve complete reaction and is controlled in conjunction with the pressure and in a manner sufficient to avoid vaporization and loss of the essential liquid components of the reaction admixture (e.g., excluding by-product alcohol).

Thus, while any effective temperature may be employed, it is contemplated that such effective temperatures typically will be at least 5° C., preferably at least 10° C., and most preferably at least 15° C., and can vary typically from about 5° to about 200° C., preferably from about 10° to about 150° C., and most preferably from about 15° to about 100° C.

The precursor forming reaction time is selected in conjunction with the reaction temperature and the amounts of Hydrocarboxides I and II to permit substantially complete reaction at the above reaction temperatures. Such reaction times typically will vary from about 0.15 to about 40 hours, preferably from about 0.2 to about 30 hours, and most preferably from about 0.5 to about 20 hours, as measured from the initiation of contact of all of the reactive components of the admixture. It is desired to conduct admixture of Hydrocarboxides I and/or II with the acidic phosphorus oxygen compound to permit a slow reaction therebetween. This is typically achieved by controlling the addition times thereof to be between about 0.5 and about 15 hours. The reaction generally will be substantially complete after typically from about 0.3 to about 10, preferably from about 0.5 to about 8, and most preferably from about 0.5 to about 5 hours, measured from completion of the formation of the reaction admixture at ambient temperature. Higher reaction temperatures will cause completion of the reaction in shorter times.

The reaction pressure is not critical provided undue loss of the liquid contents of the reaction admixture is avoided, and can be atmospheric, subatmospheric or superatmospheric.

While not critical, upon passage of the aforedescribed reaction times and apparent completion of the reaction, it is preferred to allow the contents of the admixture to age for periods of typically from about 1 to about 30 hours, and preferably from about 2 to about 22 hours, e.g., at reaction temperatures of typically from about 10° to about 100° C. to assure that complete reaction has occurred.

Upon completion of the reaction and optional aging the catalyst precursor is separated from the organic medium. Generally, the organic medium is selected so that the catalyst precursor is insoluble therein at room temperature. Thus, precursor separation can be accomplished in a variety of ways. Typically, it takes place in two stages, namely, by bulk separation and then final purification, e.g., by drying.

Bulk separation can be accomplished by filtering the reaction admixture to recover the catalyst precursor as a filter cake, by centrifuging the reaction admixture, and separating, e.g., by decanting, the supernatant liquid organic medium from the solid precursor, or by evaporating the liquid organic medium to form a cake or paste of the catalyst precursor.

The precursor solids, after bulk separation, are then typically subjected to conditions sufficient to remove any residual liquid organic medium or any organic contaminants. This can be achieved by drying, preferably continuous drying, to evaporate residual organic liquid medium, by washing the precursor solids with water or with an organic medium, preferably an organic medium, having a higher vapor pressure than the organic medium employed to form the admixture to facilitate drying, or by employing both procedures. Thus, before final purification is conducted, the separated catalyst precursor solids can be washed in a liquid organic medium one or more times to remove any residual unreacted materials and/or any other organic soluble species followed by a repetition of bulk separation procedures and then drying, although this is not required.

Drying can be achieved by heating the precursor, e.g. by exposing the precursor to air at a temperature of from about 20° to about 160° C. for a period of from about 0.5 to about 30 hours or by placing it in a forced circulation oven maintained at a temperature typically between about 40° and about 250° C. for about 0.5 to about 30 hours. Alternatively, the precursor can be air dried at room temperature for between about 1 to about 40 hours and then placed in the forced circulation oven until constant weight is attained. Drying under reduced pressure at room or elevated temperature, such as by using a vacuum oven is preferred.

The isolated precursor composition is then calcined to form the final composition capable of catalyzing the formation of $\alpha,\beta$-unsaturated products described herein. Calcination can be conducted in a separate step or in-situ in the reactor and involves heating the precursor composition to a selected temperature or temperatures within a defined temperature range. Preferably the calcination procedure is conducted in stages by heating the precursor in a stepwise fashion at increasingly higher temperature plateaus until a temperature of at least about 700° C. is attained.

Accordingly, and in view of the above, calcination is conducted at temperatures of typically from about 600° to about 1300° C., preferably from about 650° to about 1000° C. (e.g. 650° to 850° C.), and most preferably from about 700° to about 1000° C. (e.g. 700° to 950° C.) for a period of typically from about 1 to about 48 hours, preferably from about 2 to about 30 hours, and most preferably from about 2.5 to about 20 hours. Most preferably, the final temperature plateau during calcination will be at least 720° to about 950° C. for a period of about 0.5 to about 30 (e.g. 2 to 20) hours.

However, it is preferred to subject the precursor to a precalcination procedure by heating it at temperatures of typically from about 400 to about 599 and most preferably from about 450° to about 599° C., for periods of typically from about 0.1 to about 10, and preferably from about 0.5 to about 8 hours. Calcination and precalcination can be conducted as two different steps as by heating first at a selected precalcination temperature and then at a selected calcination temperature or by gradually increasing the temperature from a precalcination range to a calcination range.

The atmosphere under which calcination is conducted includes oxygen or an oxygen containing gas such as air, nitrogen, helium, or other inert gas. At the higher calcination temperatures it is preferred to include oxygen in the calcination atmosphere.

While not essential, it is preferred that the calcination atmosphere be passed as a moving gaseous stream over the precursor composition.

Calcination can be conducted before, after, or during intermediate stages of shaping of the catalyst precursor as described hereinafter.

The catalyst precursor or catalyst itself is adaptable to use in the various physical forms in which catalysts are commonly used as particulate or powdered material in a contact bed, as a coating material on monolithic structures generally being used in a form to provide high surface area, as spheres, extrudates, pellets and like configurations. The precursor or catalyst, can if desired, be composited with various catalyst binder or support materials, or physical property modifiers such as attrition resistance modifiers, which do not adversely affect the catalyst or the reactions in which the catalyst is to be employed.

Thus, various sized powders can be produced by grinding the catalyst to the desired size by any conventional or convenient means. Extrudates and pellets of various sizes and shapes can be prepared by using any conventional or convenient means. Utilizing a conventional screw type extruder, the dough or paste is processed through a die plate generally comprising orifice openings in the 1/32-½ inch diameter range to form generally cylindrical particles. The freshly extruded material may be collected in the form of strands of indefinite or random lengths to be dried and subsequently broken into extrudate particles; or the freshly extruded material may be cut into random or predetermined lengths of from about ¼ inch to about ½ inch and subsequently dried; or the freshly extruded material may be formed into spheres, for example, by the process whereby the extrudate strands are collected in a spinning drum, the strands becoming segmented and spheroidized under the spinning influence of the drum.

While the above description of the method of preparing the catalysts of the present invention is provided with respect to the minimum components which must be employed therein, it is contemplated that such catalysts may have other additives (e.g. which modify the catalyst properties) or promoters incorporated therein which typically enhance the rate and/or selectivity of the intended reaction for which the catalyst will eventually be employed to catalyze. A preferred promoter for this purpose is boron. Catalysts of the present invention which contain boron exhibit slightly better activity at lower reaction temperatures when employed to catalyze the synthesis of the $\alpha, \beta$-ethylenically unsaturated products described herein. Boron can be incorporated into the catalyst composition during preparation of the catalyst precursor or by impregnation of the catalyst precursor or catalyst with a suitable boron compound prior or subsequent to calcination procedures. Preferably, the boron compound is incorporated during preparation of the catalyst precursor. This can be achieved by selecting a suitable boron compound which preferably is soluble in the liquid organic medium. Representative examples of such boron compounds include boron acetate, boron hydrocarboxides, preferably boron alkoxides, wherein the hydrocarboxide portion is as described in connection with hydrocarboxides I and II, bis (di-acetoboron) oxide, boric acid, and mixtures thereof. The boron compound can be added to the precursor forming admixture directly or to any of the solutions which are combined to form the precursor forming admixture.

Alternatively, a boron compound can be impregnated into the catalyst composition by conventional means, such as by contact of the catalyst composition with an impregnating solution having the boron compound dissolved therein. Compounds of titanium, such as, $TiO_2$ or titanium hydrocarboxide similar to the hydrocarboxides disclosed herein, can also be included in the catalyst in a similar manner.

The catalysts of the present invention have a surface area of typically from about 40 to about 300, and preferably from about 50 to about 170 m$^2$/g, as determined by the BET method, the general procedures and theory for which are disclosed in H. Brunaur, P. Emmett and E. Teller, J. of Am. Chem. Soc. Vol. 60, p. 309 (1938).

When aluminum and silicon are employed in Hydrocarboxides I and II respectively, the resulting catalysts are characterized by an x-ray diffraction pattern that distinguishes them from (a) crystalline AlPO$_4$, and (b) a mixture of crystalline AlPO$_4$ and amorphous silica gel, i.e., the primary distinguishing peaks of materials (a) and (b) immediately above are absent from the x-ray spectra of the Al/Si/P/O catalysts of the present invention. Furthermore, in most instances, the Al/Si/P/O catalysts of the present invention exhibit x-ray spectra characterized by the absence of any distinct crystalline phases, i.e., they are substantially amorphous within the limits of detection of the x-ray diffraction technique. This is true for materials calcined at temperatures of at least 520° C. In some instances, however, a single low intensity, but distinct peak is observed, indicative of the presence of a very minor amount of crystalline material. However, this peak is not present in the x-ray spectra of materials (a) and (b) above.

The catalysts of the present invention can be employed to improve any one or more of the rate, conversion and selectivity of the following well known reaction types:

(1) The condensation, e.g., vapor phase condensation, of at least one aldehyde, or aldehyde forming compound, i.e., aldehyde precursor (e.g. methylal), with at least one carboxylic acid or derivative thereof, such as an ester, to form α, β-unsaturated acids or esters. Such reaction can be represented by the following equation:

(eq. 3)

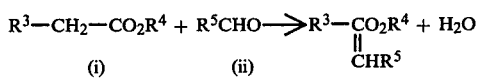

wherein R$^3$, R$^4$, and R$^5$ which may be the same or different represent hydrogen, or a hydrocarbyl radical as described in conjunction with the unsubstituted R group of formula II described hereinabove. Since these reactions are conducted in the vapor phase, the identity of hydrocarbyl groups R$^3$, R$^4$, and R$^5$ is selected so that the respective reactants are vaporizable without substantial decomposition under reaction conditions. Reactant (ii) of eq. 3 can alternatively be replaced with acetals (e.g., methylal), or hemiacetals represented by the structural formula R$^5$-CH(OR$^4$)$_2$ and R$^5$-CH(OH)OR$^4$.

(2) The condensation, e.g., vapor phase condensation, of at least one carbonyl containing compound with at least one aldehyde, acetal, and/or hemiacetal to form at least one α, β-unsaturated product as represented by the following reactions:

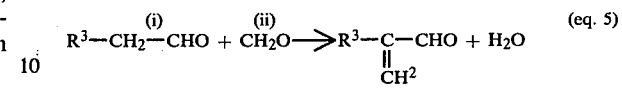

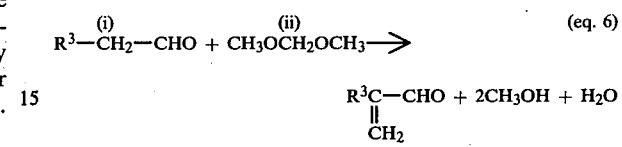

wherein R$^3$ is as described above.

(3) The esterification or hydrolysis of an ester as represented by the following reversible reaction:

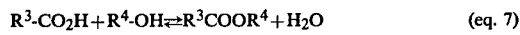

wherein R$^3$ and R$^4$ are as described above.

(4) The conversion of an alcohol to an ether or hydrolysis of the ether to an alcohol as represented by the reversible reaction:

wherein R$^3$ is as described above.

(5) The reaction of an ether with a carboxylic acid to form an ester and alcohol as represented by the reaction:

(6) Other organic reactions which can be catalyzed by acidic catalysts, such as dehydration, isomerization, alkylation, cracking and the like.

Representative examples of suitable esters which can be employed in the reaction of equation 3 include methyl acetate, ethylacetate, methyl propionate, ethyl propionate, methyl n-butyrate and the methyl ester of phenyl acetic acid. Representative acids which can be employed in the reaction of the above equations include the corresponding free acids of the above identified esters.

If formaldehyde is employed as a reactant in any of the aforedescribed reactions, particularly equations 3 and 4 it can be used in any convenient form. For example, it can be anhydrous paraformaldehyde, trioxane or in the form of an aqueous of alcoholic solution as are available commercially. If desired, the process may be coupled directly with a process for the manufacture of formaldehyde or its polymers.

Processes for the production of α, β-unsaturated products in accordance with the reaction of equations 3 to 6 are well known as described hereinafter. Thus, starting materials (i) and (ii) of equations 3 to 6 are employed in stoichiometric amounts, or in excess of either one over the other. Accordingly, the mole ratio of starting materials (i) and (ii) of equations 3 to 6 typically can vary from about 100:1 to 1:1.5, preferably from about 50:1 to about 1:1, and most preferably from about 10:1 to about 2:1.

The above reactions are preferably conducted in the vapor phase in the presence of the catalyst of the present invention, continuously or batchwise, in a fixed or fluid bed. The catalyst may be charged to a tube or on trays or in a fluid bed, etc. through which the reactant mixture is passed. The reactor system may consist of a series of catalyst beds with optional interstage heating or cooling between the beds if desired. It is also an embodiment of the invention to use either upflow or downflow of the reactants through the reactor, with periodic reversal of gas flow also being contemplated to maintain a clean catalyst bed. If desired the gaseous feed may be charged together with an inert carrier gas, e.g., nitrogen, helium, argon, carbon oxides or low molecular weight hydrocarbons.

The reaction temperature of the above reactions (eq. 3 to 6) will typically vary from about 170 to about 450, preferably from about 200 to about 400, and most preferably from about 250° to about 380° C., under atmospheric or superatmospheric pressure (e.g. 1 to 150 psig).

Suitable feed rates of reactants to the reaction zone typically can vary from about 0.2 to about 20, preferably from about 0.4 to about 10, and most preferably from about 0.5 to about 5 hr.$^{-1}$ LHSV.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, unless otherwise specified, each catalyst is tested in the following manner: A glass tube reactor 20 inches in length, 1 inch O.D. and about 0.8 inch I.D., is stoppered at the bottom with glass wool, loaded with 20 cc of catalyst sample, on top of which is placed 10 cc of glass wool, followed by the addition of a sufficient number of 4 mm diameter glass balls to fill the remaining reactor tube volume. The glass balls serve as a preheating zone about 7 inches in length within the tube. The reactor is then mounted in a vertical furnace having a heating chamber 2.5 cm in diameter and 30.5 cm in length. A liquid reactant feed stream is then passed downward through the reactor tube at a selected furnace temperature as described herein. The feed stream is vaporized in the preheating zone and contacts the catalyst as a vapor. All reactions are carried out under ambient atmospheric pressure. The reactant feed stream is passed through the reactor at a liquid hourly space velocity (LHSV) of 1 hr$^{-1}$, i.e., the liquid feed is pumped through the reactor at a rate sufficient to displace 1 empty reactor volume of liquid every hour. The reactor effluent for the first 15 minutes after each start-up is discarded, but is collected thereafter for a period of 2.5 hours in an ice trap. The total liquid effluent collected during this time is analyzed by gas chromatography, mass spectrophotometry, and NMR. Analysis for formaldehyde, other aldehydes, and ketones is conducted by reacting the respective reaction products with o-benzylhydroxylamine hydrochloride and sodium acetate, said reaction being conducted in the presence of at least 55%, by weight methanol based on the weight of the mixture. Unless other specified, the liquid reactant feed stream comprises 10%, by weight, methylal and 90%, by weight, methyl propionate, based on the total weight of the feed stream, and total conversion of methylal, selectivity, and yield are calculated as follows:

$$\text{Methylal Conversion (\%)} = \frac{A - B}{A} \times 100$$

$$\text{Selectivity to MMA + MA \% (S}_1) = \frac{C}{A - B - D} \times 100$$

$$\text{Selectivity to formaldehyde (\%) (S}_2) = \frac{D}{A - B} \times 100$$

$$\text{Yield of MMA + MA (\%)} = \frac{C}{A} \times 100$$

$$\text{Yield of MMA + MA + F (\%)} = \frac{C + D}{A} \times 100$$

wherein the above equations:
A = moles of methylal in feed.
B = moles of methylal in reaction product.
C = moles of MMA + MA in reaction product.
D = moles of formaldehyde in reaction product.
F = formaldehyde.
MMA = methyl methacrylate.
MA = methacrylic acid.

In some examples methyl propionate is replaced with equal wt. %'s of propionic acid. Also, in some instances methylal is replaced by formcel, and the moles of methylal are replaced by moles of formcel in the above calculations.

EXAMPLE 1

Two solutions were prepared. In the first solution 155.15 g of tetraethyl orthosilicate (Si(OC$_2$H$_4$)$_4$) and 115 g of aluminum tri-sec-butoxide (Al(OC$_4$H$_9$)$_3$) were dissolved in 1100 cc of acetone. The second solution was prepared by dissolving 50.25 g of an 85% aqueous solution of H$_3$PO$_4$ and 45.61 g of water in 250 cc of acetone. The second solution was slowly added at 25° C. to the first solution over a period of 5 hours with continuous vigorous mechanical stirring. After completion of the addition, the reaction mixture was allowed to age at room temperature overnight (i.e. 18 hours) with mechanical stirring. A white precipitate was separated from the reaction mixture by filtration and the precipitate dried in air at 98° C. overnight in a vacuum oven. The dried solid was then calcined in air 400° C. for 1.5 hours, 450° C. for 1 hour, and then 560° C. for 3 hours. The calcined product was ground to a powder −16 mesh (Tyler sieve series). The powder, 46.54 g, was mixed with 23 g water and pelletized to 0.5 inch diameter pellets. The pellets were then calcined in air at 150° C. for 1 hour, 400° C. for 30 minutes, 520° C. for 30 minutes, and then 750° C. for 3 hours. The calcined pellets were ground to −6+16 mesh granules and 20 cc (8.42 g) of the catalyst were tested as described above at a furnace temperature of 350° C. Another 20 cc of catalyst were also tested at a furnace temperature of 370° C. The results are summarized at Table 1, Run 1 (furnace temp. 350° C.) and Run 2 (furnace temp. 370° C.).

EXAMPLE 2

Two solutions were prepared in general accordance with Example 1, using 150.5 g of aluminum tri-sec-butoxide, 152.3 g tetraethyl orthosilicate, and 1400 cc acetone for solution 1, and 66.99 g of 85% aqueous H$_3$PO$_4$ solution, 42.62 g water, and 350 cc of acetone for solution 2. Only 60 volume % of solution 2 was slowly added to solution 1 to form the reaction mixture under continuous vigorous mixing. At this point 140 cc of acetone were added to the continuously stirred reaction mixture followed by addition of the remaining 40 volume % of solution 2. About 5 hours were required for completion of the addition of solution 2 to solution 1. The reaction mixture was then aged overnight with mechanical stirring. A white precipitate was separated from the reaction mixture by filtration and dried at 90°–110° C. overnight in a vacuum oven. The dried solid was then calcined in air at 400° C. for 1 hour, 500° C. for 1 hour, and then 540° C. for 4 hours. The calcined product was ground to a powder (+16 mesh) and 21.23 g of this powder mixed with 2.02 g water soluble starch and 14.74 g water. The resulting mixture was pelletized and the pellets (0.5 inch diameter) calcined at 400° C. for 35 minutes, 450° C. for 1.5 hours, and then 600° C. for 2.5 hours in air. The calcined pellets were ground to −6+16 mesh granules and the granules calcined at 750° C. for 4 hours in air. Only part of these granules were further calcined at 820° C. for 4.5 hours and then 880° C. for 3.5 hours. From each of the alternatively calcined catalyst samples were removed 20 cc, i.e., 8.70 g of Sample A calcined to a maximum of 750° C., and 8.86 g of Sample B calcined to a maximum of 880° C. Each sample was placed in a reactor and tested as described above. The results are summarized at Table 1, Run 3 (Sample A) and Run 4 (Sample B).

EXAMPLE 3

Two solutions were prepared in general accordance with Example 1 using 133.0 g aluminum tri-sec-butoxide, 176.73 g tetraethyl orthosilicate, and 1400 cc acetone for solution 1, and 59.20 g of the 85% aqueous $H_3PO_4$ solution, 52.22 g water, and 350 cc acetone for solution 2. About 90 volume % of solution 2 was slowly added to solution 1 at room temperature for a period of about 5 hours while mixing vigorously to form a reaction mixture. The resulting reaction mixture was refluxed while adding the remaining 10 volume % of solution 2; and the refluxing continued for 1.5 hours after completion of the addition. The reaction mixture was cooled to room temperature and aged overnight with mechanical stirring. A white precipitate was separated from the reaction mixture by the filteration and the filter cake dried overnight at 90°–120° C. in a vacuum oven. The dried filter cake was calcined at 400° C. for 1.5 hours and then 520° C. for 4 hours in air. The calcined product was ground to a powder (+16 mesh) and 28.73 g thereof mixed with 0.86 g of water soluble starch and then 11.3 g water. The mixture was pelletized and the pellets (0.5 inches diameter) calcined at 430° C. for 1.6 hours, 600° C. for 1.5 hours, and then 670° C. for 2 hours in air. The calcined pellets were ground to −6+16 mesh granules and the granules further calcined at 750° C. for 3 hours in air. A sample of 20 cc (6.49 g) of the calcined catalyst was tested as described herein and the results summarized at Table 1, Run 5.

EXAMPLE 4

Two solutions were prepared in general accordance with Example 1, using 112.90 g aluminum tri-sec-butoxide, 186.63 g tetraethyl orthosilicate, and 1400 cc acetone for solution 1, and 50.25 g of the 85% aqueous $H_3PO_4$ solution, 58.03 g water, and 350 cc acetone for solution 2. Solution 2 was added to solution 1 to form the reaction mixture in accordance with Example 1, with the exception that after the addition of 60 volume % of solution 2, 150 cc of acetone was slowly added to the reaction mixture, and the addition of further solution 2 resumed until 93 volume % of Solution 2 has been added. At this time the reaction mixture was refluxed and the remainder of solution 2 added while the reaction mixture was refluxing. The reflux was continued for an additional 1.2 hours after completion of the solution 2 addition. The reaction mixture was cooled to room temperature, aged overnight with mechanical stirring and then refluxed for an additional 3 hours. The white precipitate was separated from the reaction mixture by the filtration and the filter cake dried at 116° C. overnight in a vacuum oven. The dried solid was then calcined at 440° C. for 1.5 hours and 520° C. for 5 hours in air. The calcined filter cake was ground to a powder (+16 mesh) and 30.99 g of the powder sample were mixed with 1.48 g of water soluble starch and then 10.20 g water. The mixture was pelletized and the pellets (0.5 inch diameter) were calcined at 450° C. for 50 minutes, 600° C. for 1.5 hours, and 670° C. for 2.7 hours in air. The calcined pellets were ground to −6+16 mesh granules, further calcined at 750° C. for 4 hours, 820° C. for 4 hours, and 880° C. for 4 hours in air. A sample of 20 cc (7.00 g) of the calcined catalyst was tested as described herein and the results summarized at Table 1, Run 6.

EXAMPLE 5

In general accordance with Example 1, two solutions were prepared using 138.56 g tetraethyl orthosilicate, 59.10 g aluminum tri-sec-butoxide, and a mixture of 908 g of diethyl ether and 400 cc of acetone for solution 1, and 26.86 g of the 85% aqueous $H_3PO_4$ solution, 28.03 g water and 200 cc of acetone for solution 2. In addition, a third solution was prepared by dissolving 23.64 g of aluminum tri-secbutoxide in 200 cc of diethyl ether; and a fourth solution was prepared by dissolving 10.74 g of the 85% aqueous $H_3PO_4$ solution and 12.49 g of water in 100 cc of acetone. Solution 2 was then gradually added to solution 1 over a period of about 3.5 hrs. at room temperature while stirring vigorously, to form a reaction mixture. Solution 3 was then slowly added to the continuously agitated reaction mixture over a period of 5 min; and the reaction mixture stirred for an additional 30 minutes upon completion of the solution 3 addition. Solution 4 was then slowly added to the continuously agitated reaction mixture over a period of 1 hr. The reaction mixture was then aged for 18 hours at room temperature under continuous agitation with a magnetic stirrer. The aged reaction mixture was then refluxed for 2.17 hours, cooled to room temperature, and the white precipitate separated from the reaction mixture by filtration. The filter cake was dried at 116° C. for 2 days in a vacuum oven and then calcined at 450° C. for 1 hour, and 520° C. for 4.5 hours in air. The calcined filter cake was ground to a powder (+16 mesh) and 46.36 g thereof, mixed with 1.3 g of water soluble starch, and then 4.98 g water. The mixture was pelletized and the pellets (0.5 inch diameter) calcined at 460° C. for 1 hour, and 600° C. for 17 hours in air. The calcined pellets were ground to −6+16 mesh granules, and the granules further calcined at 750° C. for 16 hours, and 830° C. for 4.5 hours. The so calcined granules were then divided into two separate samples, i.e., samples A and B. Only sample B was further calcined in air at 880° C. for 4.5 hours. Then 20 cc portions of samples A (5.80 g) and B (5.20 g) were tested as described herein, and the results summarized at Table 1, Run 7 (Sample A) and Run 8 (Sample B).

EXAMPLE 6

Two solutions were prepared in general accordance with Example 1 using 116.53 g tetraethyl orthosilicate, 116.1 g aluminum tri-sec-butoxide, and 1500 cc of 1,2-dimethoxyethane solvent for solution 1, and 52.76 g of the 85% aqueous $H_3PO_4$ solution, 29.18 g water, and 250 cc 1,2-dimethoxyethane solvent, for solution 2. Solution 2 was added to solution 1 in accordance with Example 1 to form the reaction mixture. After aging the reaction mixture at 25° C. for 18 hours with mechanical stirring, and then refluxing the same for 2 hours, the white precipitate was separated from the reaction mixture by filteration. The filter cake was dried at 129° C. overnight in a vacuum oven and the dried filter cake calcined at 460° C. for 1.5 hours, and 520° C. for 4.5 hours in air, ground to a powder (+16 mesh), and 40.84 g thereof mixed with 1.23 g of water soluble starch, and then 5.95 g water. The mixture was pelletized, and the pellets (0.5 inch diameter) calcined at 460° C. for 1 hour, and then 600° C. for 17 hours in air. The calcined pellets were ground to −6+16 mesh granules and the granules further calcined at 750° for 5 hours in air. A sample of 20 cc (7.02 g) of the catalyst was tested and the result summarized at Table 1, Run 9.

EXAMPLE 7

Two solutions were prepared in general accordance with Example 1 using 110.33 g tetraethyl orthosilicate, 100.45 g aluminum tri-sec-butoxide, 25.5 g germanium tetraethoxide, and a mixture of 908 g absolute diethyl ether and 500 ml of acetone for solution 1, and 45.64 g of the 85% aqueous $H_3PO_4$ solution, 36.50 g water, and 250 cc acetone for solution 2. Solution 2 was added to solution 1 in accordance with Example 1 to form a reaction mixture. The reaction mixture was then aged for 18 hours at 25° C. with mechanical stirring followed by refluxing of the same for 2.5 hours. The white precipitate was separated from the reaction mixture by filteration, and the filter cake dried at 116° C. for 2 days in a vacuum oven. The dried material was then calcined at 460° C. for 1 hour, and 520° C. for 6 hours in air. The calcined filter cake was ground to powder (+16 mesh) and 44.72 g thereof mixed with 1.34 g of water soluble starch, and then 4.49 g $H_2O$. The mixture was pelletized and the pellets (0.5 inch diameter) calcined at 460° C. for 1.5 hours, and 600° C. for 11.5 hours in air. The calcined pellets were ground to −6+16 mesh granules and the granules further calcined at 750° C. for 4.5 hours, and 820° C. for 4.5 hours in air, and 20 cc (7.0 g) of the catalyst sample were tested and the results summarized at Table 1, Run 10.

EXAMPLE 8

Two solutions were prepared in general accordance with Example 1 using 141.99 g of tetraethyl orthosilicate, 42.41 g of titanium tetrabutoxide, 142.41 g of aluminum tri-sec-butoxide, and 1150 cc of acetone for solution 1, and 62.23 g of 85% aqueous $H_3PO_4$ solution, 48.20 g of water and 300 cc of acetone for solution 2. The two solutions were combined in accordance with Example 1 to form a reaction mixture. The reaction mixture was then aged for 18 hours at separated from the reaction mixture by filtration, the filter cake dried at 100° C. overnight in a vacuum oven, and then calcined at 400° C. for 1.5 hours, 500° C. for 1 hour, and 560° C. for 3 hours in air. The calcined product was ground to a powder (+16 mesh) and 40.5 g thereof mixed with 7 g of water and then pelletized. The pellets (0.5 inch diameter) were calcined at 120° C. for 1.5 hours, 300° C. for 1 hour, and 750° C. for 3 hours in air. The calcined product was ground to −6+16 mesh granules and 20 cc (10.40 g) of the catalyst sample tested as described herein. The results are summarized at Table 1, Run 11.

EXAMPLE 9

A 13.56 g sample of the +16 mesh powder sample obtained from Example 5 after calcination of the filter cake at 520° C. for 4.5 hours but prior to pelletizing, was mixed with 0.41 g of water soluble starch and 2.24 g water. The mixture was pelletized and the pellets (0.5 inch diameter) calcined at 460° C. for 1 hour, and then 600° C. for 17 hours in air. The pellets were ground to −6+16 mesh granules and the granules further calcined at 820° C. for 5.5 hours, 880° C. for 4.5 hours, and then 930° C. for 4.5 hours in air. A 20 cc (6.07 g) catalyst sample was tested and the results summarized at Table 1, Run 12.

EXAMPLE 10

Two solutions are prepared in general accordance with Example 1 using 137.71 g of tetraethyl orthosilicate, 57.21 g aluminum tri-sec-butoxide and a mixture of 1050 cc of diethyl ether and 500 cc of acetone for solution 1, and 26.34 g of an 85% aqueous $H_3PO_4$ solution, 25.54 g water and 200 cc acetone for solution 2. A third solution was prepared by dissolving 25.43 g aluminum tri-sec-butoxide in 150 cc of acetone, and a fourth solution was prepared by mixing 11.56 g of an 85% aqueous $H_3PO_4$ solution with 12.64 g water and 100 cc of acetone. Solution 2 was added slowly to solution 1 in accordance with Example 1 to form a reaction mixture. Solution 3 was then added slowly to the reaction mixture at 25° C. over a period of 5 min. and the contents thereof stirred for 0.97 hours from completion of addition. Solution 4 was then slowly added to continuously agitated reaction mixture over a period of 1 hour, and the contents thereof refluxed for 1.13 hours from completion of the addition. The reaction mixture was cooled to room temperature and aged overnight with mechanical stirring. A white precipitate was separated from the reaction mixture by filtration and the filter cake dried at 116° C. overnight in a vacuum oven. The dried filter cake was calcined at 450° C. for 1 hour, and 528° C. for 4 hours in air. The calcined filter cake was ground to a powder (+16 mesh) and 28.92 g thereof mixed with 1.0 g of water solution starch and then 8.3 g water. The mixture was pelletized and the pellets (0.5 inch diameter) calcined at 450° C. for 1 hour, and 600° C. for 3.3 hours in air. The calcined pellets were ground to granules (−6+16 mesh) and the granules further calcined at 600° C. for 1 hour, 750° C. for 4 hours, 820° C. for 4.5 hours, and 880° C. for 4 hours in air. A 20 cc (6.34 g) catalyst sample was tested for the condensation reaction between methylal and propionic acid. The reaction was carried out at 350° C. furnace temperature and 1 LHSV with a feed solution of 10 wt.% methylal in propionic acid. The product analysis showed a total methylal conversion of 100%, yield of MA+MMA of 62.2%, yield of formaldehyde of 23.3%, a combined yield of MA, MMA and formaldehyde of 85.5%.

This example illustrates the effect of replacing methyl propionate with propionic acid, namely, selectivity to MMA+MA drops only slightly, relative to the use of methyl propionate. Thus, the free acid is a sutiable alternative to the corresponding ester.

EXAMPLE 11

Upon completion of catalyst testing of Sample B from Example 2, this catalyst was re-calcined at 600° C. for 1 hour, and then 920° C. for 4.5 hours. A sample of 20 cc (9.19 g) of this material was tested as a catalyst for the condensation reaction between the methyl hemiacetal of formaldehyde and methyl propionate (known as methyl formcel and comprising about 35 wt.% methanol, 55 wt.% formaldehyde and 10-11 wt.% $H_2O$). Thus, 54.45 g of methyl formcel was mixed with 669.6 g of methyl propionate and the mixture was used for catalyst testing in accordance with the procedures described hereinabove. The reaction was carried out at 350° C. furnace temperature and 1 hr.$^{-1}$ LHSV. The product analysis showed a yield to MMA+MA of 64.0%, at a total conversion of methyl formcel of 80%. This example illustrates that the methyl hemiacetal of formaldehyde is a suitable replacement for methylal in the feed stream.

EXAMPLE 12 (Part A)

Upon completion of Example 8, the catalyst employed therein was re-calcined at 600° C. for 1 hour, and then 820° C. for 4.5 hours in air. A 20 cc (6.96 g) sample thereof was loaded in a glass tube reactor. After placing the reaction in a vertical furnace, the furnace was heated to 350° C. and then a solution of a mixture of methyl propionate (75.41 wt.%), propionic acid (9.11 wt.%), and methanol (15.48 wt.%) was pumped into the reactor at a 1 hr.$^{-1}$ LHSV feed rate. The analysis of the reactor effluent showed that decarboxylation of methyl propionate and/or propionic acid did not occur to any detectable extent. After this reaction, the catalyst was heated at 350° C. for 3.5 hours in a $N_2$ gas flow and then the following experiment was carried out.

(Part B)

The furnace was heated to 320° C., and a solution of a mixture of 35.05 wt.% diethyl ether, and 64.95 wt. % propionic acid, was pumped into the reactor at a 1 hr.$^{-1}$ LHSV feed rate. The product analysis showed 38.7 mole % propionic acid conversion to ethyl propionate and again there was no indication of any decarboxylation of propionic acid and/or ethyl propionate. Part B of this example illustrates the use of the catalyst of the present invention to catalyze Equation 9 described hereinabove.

EXAMPLE 13

Two solutions were prepared in general accordance with Example 1, using 118.1 g aluminum tri-sec-butoxide, and 188.6 g tetraethyl orthosilicate dissolved in 1400 cc acetone for solution 1 and 52.57 g 85% aqueous $H_3PO_4$ solution, 57.34 g $H_2O$, and 360 cc acetone for solution 2. At room temperature 88.2% of solution 2 was slowly added to solution 1 in accordance with Example 1 with vigorous stirring. The remaining 11.8 wt.% of solution 2 was added to the resulting mixture while refluxing the latter. The reflux was continued for 1.5 hours after completing the addition of solution 1. The reaction mixture was cooled to room temperature and aged 1.5 days with mechanical stirring. White precipitate was separated from the reaction mixture by the filtration, the filter cake dried at 115° C. in a vacuum oven, and then calcined at 430° C. for 2 hours, and 520° C. for 4 hours in air. The calcined filter cake was ground to −20+48 mesh powder. This powder was pelletized without using water and starch. Pellet size was ⅛×⅛". The pellets were calcined at 600° C. overnight, 750° C. for 5.5 hours, 820° C. for 6 hours, and then 880° C. for 5.5 hours in air.

A 20 cc (7.4 g) catalyst sample was loaded in the reactor and tested as described herein in three different runs at varying feed rates and furnace temperatures as described in Table 1. The results are summarized at Table 1, Runs 26 to 28.

COMPARATIVE EXAMPLE 1

This comparative example is intended to illustrate the performance of a typical acidic catalyst disclosed in U.S. Pat. No. 4,118,588. Thus, 75 g $TiO_2$ (anatase) powder, 57.5 g $AlPO_4$ powder, and 18.7 g $H_3BO_3$ powder were mixed and the mixture mixed with 48.2 g aqueous urea solution, which had been prepared by dissolving 37.5 g urea in 100 g dionized water, to form a thick paste. The paste was dried at 120° C. for 3 hours and then calcined at 600° C. for 3 hours. The calcined paste was ground to −6+16 mesh granules.

A 20 cc (15.89 g) catalyst sample was loaded into a glass reactor, and after placing the reactor in a verticle furnace, a feed stream containing 10 wt.% methylal solution in methyl propionate was passed through the reactor at a flow rate of 1 hr.$^{-1}$ LHSV at furnace temperatures of 350°, 370°, and 390° C. Product samples were removed at each reaction temperature, and analyzed as described hereinabove. The results are summarized at Table 2, Runs 14 to 16.

COMPARATIVE EXAMPLE 2

This example is intended to illustrate the performance of a conventional basic catalyst such as also disclosed in U.S. Pat. No. 4,118,588. Thus, 60 g of $AlPO_4$ powder was mixed with 4.35 g LiOH powder. The resulting mixture was mixed with 85.91 g water at about 90° C. to evaporate water and form a solid mass. The solid mass was further dried at 210° C. for 1.5 hours, and then calcined at 520° C. for 3 hours. The calcined mass was ground to −6+16 mesh granules. A 20 cc (11.82 g) sample thereof was then loaded into the glass reactor and tested in accordance with Comparative Example 1 using the same feed stream recited therein and a furnace temperature of 350° C. (Run 17) and 370° C. (Run 18).

COMPARATIVE EXAMPLE 3

This example is intended to illustrate the performance of a basic catalyst on the silica gel support such as illustrated in U.S. Pat. No. 3,100,795 but using methylal instead of formaldehyde. Thus, 0.65 g of KOH was dissolved in 225 g of water and 53.80 g of silica gel (−8+12 mesh, 300 $m^2/g$ surface area and 1 cc/g pore volume) was impregnated with this KOH solution.

A 20 cc sample of the impregnated product was loaded in a glass reactor and subjected following thermal treatment in $N_2$ flow (800 cc/min) prior to the catalyst test:
 200° C.: 1 hour
 350° C.: 30 minutes
 435° C.: 5 hours Catalyst testing was carried out at 370° C. (Run 19) and 420° C. (Run 20) furnace temperatures, in accordance with Comparative Example 1 and the results summarized at Table 2, Runs 19 and 20.

COMPARATIVE EXAMPLE 4

This example is intended to illustrate the performance of an acidic catalyst such as described in the Albanesi et al article described above. Thus, 36.87 g of the silica gel used in Comparative Example 3 was impregnated with tungstic acid solution prepared by mixing 5.04 g tungstic acid powder with 400 ml water. The impregnated product was calcined at 410° C. for 13.5 hours, 600° C. for 5 hours, and then 880° C. for 6.5 hours. A 20 cc sample thereof was tested in accordance with Comparative Example 1 at a furnace temperature of 350° C. and product sample removed and analyzed as described herein and the results summarized at Table 2, Run 21.

COMPARATIVE EXAMPLE 5

This example is intended to illustrate the criticality of Hydrocarboxide II to catalyst composition of the present invention, by omitting tetraethyl orthosilicate therefrom. Accordingly, two solutions were prepared in general accordance with Example 1 using 250 g of aluminum trisec-butoxide dissolved in 1150 cc acetone for solution 1, and 102.07 g of 87.8% aqueous $H_3PO_4$ solution in 250 cc acetone for solution 2. Solution 2 was slowly added to solution 1 to form a reaction mixture as per Example 1. After 12 hours from completion of the solution 2 addition, a white precipitate was separated by filteration and dried at 98° C. overnight in a vacuum oven. The dried product was calcined at 400° C. for 2 hours, and 580° C. for 3 hours in air. The calcined product was ground to a power (+16 mesh) and 26.0 g thereof was mixed with 4 g water. The mixture was pelletized (0.5 inch diameter) and the pellets calcined at 120° C. for 1 hour, 200° C. for 2.5 hours, and 600° C. for 3 hours. The calcined pellets were ground to −5+16 mesh granules. A 20 cc (9.54 g) catalyst sample was tested as in Comparative Example 1 using a furnace temperature of 350° C. and the results summarized at Table 2, Run 22.

COMPARATIVE EXAMPLE 6

This example illustrates the effect on catalyst performance of substituting a Group 4b metal alkoxide such as Ti for silicon. Accordingly, two solutions were prepared in general accordance with Example 1 using 320 g titanium tetrabutoxide, 160 g aluminum tri-sec-butoxide, and 1300 cc acetone for solution 1, and 71.20 g of 85% aqueous $H_3PO_4$ solution, 51.32 g water and 300 cc acetone for solution 2. After adding 80 volume % of solution 2 to solution 1 to form a reaction mixture as per Example 1, 3.675 g of boric acid was added to the reaction mixture under continuous agitation at 25° C., followed by the addition of the remaining 20 volume % of solution 2 to the same. After completion of the addition (total addition time being about 5 hours), the reaction mixture was aged for 18 hours at 25° C. with mechanical stirring. A white precipitate was separated from the reaction mixture by filtration and the filter cake dried at 65°–135° C. for 18 hours in a vacuum oven. The dried filter cake was calcined at 200° C. for 1 hour and then 50° C. for 4 hours in air. The calcined product was ground to a powder (+16 mesh) and 146.77 g thereof mixed with 12.48 g of water soluble starch and then 8 g water. The mixture was extruded through a 1/16 inch nozzle. The extrudate was dried and then calcined at 570° C. for 3 hours in air. A 20 cc (18.94 g) catalyst sample was tested in accordance with Comparative Example 1 at a furnace temperature of 350° C. and the results summarized at Table 2, Run 23.

COMPARATIVE EXAMPLE 7

This example illustrates the effect on the performance of a catalyst prepared by substituting a silicon ester for the silicon alkoxide in the catalyst preparative procedure. Accordingly, two solutions are prepared in general accordance with Example 1 using 190.53 g of silicon tetra acetate ($Si(OOCCH_3)_4$), 145.78 g of aluminum tri-sec-butoxide and 1450 cc of acetone, and 20.17 g bis (diacetoboron) oxide for solution 1, and 63.36 g of 85% aqueous $H_3PO_4$ solution, 42.42 g water, and 250 cc of acetone for solution 2. Solution 2 was slowly added to solution 1 as per Example 1. After completion of the addition, the reaction mixture was aged at room temperature for 18 hours with mechanical stirring. A white precipitate was separated from the reaction mixture by filteration and the filter cake dried at 90° C. for 3 hours and then at 110° C. for 18 hours in a vacuum oven. The dried filter cake was calcined at 400° C. for 1.5 hours, 450° C. for 30 minutes, and then 560° C. for 3 hours in air. The calcined cake was ground to −6+16 mesh granules and had gray color. A portion of the ground calcined cake was further calcined at 750° C. for 4.3 hours and designated Sample B. The ground catalyst calcined to a maximum temperature of 560° C. is designated Sample A. A 20 cc (15.40 g) portion of catalyst Sample A and a 20 cc (16.78 g) portion of catalyst Sample B were tested in accordance with Comparative Example 1 at a furnace temperature of 350° C. and the results summarized at Table 2, Run 24 (Sample A) and Run 25 (Sample B).

TABLE 1

| Run No. | Corresponding Ex. No. | Catalyst Forming Reactants | CATALYST TESTING CONDITIONS Reactant Feed Stream | Furnace Temp. (°C.) | Feed Rate (LHSV) | Methylal Conversion (%) | Yield of MMA + MA (%) | Selectivity of MMA + MA (%) | Selectivity of F (%) | Yield of MMA + MA + F (%) |
|---|---|---|---|---|---|---|---|---|---|---|
| 1 | 1 | $(EtO)_4$ Si<br>Al—tri-S—B<br>$H_3PO_4$<br>$H_2O$ | A | 350 | 1.0 | 100 | 54.1 | N/D | N/D | N/D |
| 2 | 1 | $(EtO)_4$ Si<br>Al—tri-S—B<br>$H_3PO_4$<br>$H_2O$ | A | 370 | 1.0 | 100 | 59.5 | N/D | N/D | N/D |
| 3 | 2 | $(EtO)_4$ Si<br>Al—tri-S—B<br>$H_3PO_4$<br>$H_2O$ | A | 350 | 1.0 | 100 | 60.4 | 96.9 | 37.7 | 98.1 |
| 4 | 2 | $(EtO)_4$ Si<br>Al—tri-S—B | A | 350 | 1.0 | 100 | 62.1 | 99.0 | 37.3 | 99.4 |

TABLE 1-continued

| Run No. | Corresponding Ex. No. | Catalyst Forming Reactants | CATALYST TESTING CONDITIONS ||||  Methylal Conversion (%) | Yield of MMA + MA (%) | Selectivity of MMA + MA (%) | Selectivity of F (%) | Yield of MMA + MA + F (%) |
|---|---|---|---|---|---|---|---|---|---|---|
| | | | Reactant Feed Stream | Furnace Temp. (°C.) | Feed Rate (LHSV) | | | | | |
| 5 | 3 | $H_3PO_4$ $H_2O$ $(EtO)_4 Si$ Al—tri-S—B | A | 350 | 1.0 | 100 | 59.1 | 90.8 | 34.9 | 94.0 |
| 6 | 4 | $H_3PO_4$ $H_2O$ $(EtO)_4 Si$ Al—tri-S—B | A | 350 | 1.0 | 100 | 59.7 | 99.0 | 39.7 | 99.4 |
| 7 | 5 | $H_3PO_4$ $H_2O$ $(EtO)_4 Si$ Al—tri-S—B | A | 350 | 1.0 | 100 | 64.1 | 87.0 | 26.1 | 90.5 |
| 8 | 5 | $H_3PO_4$ $H_2O$ $(EtO)_4 Si$ Al—tri-S—B | A | 350 | 1.0 | 100 | 68.6 | 97.7 | 29.8 | 98.4 |
| 9 | 6 | $H_3PO_4$ $H_2O$ $(EtO)_4 Si$ Al—tri-S—B | A | 350 | 1.0 | 100 | 56.3 | 94.5 | 40.5 | 96.8 |
| 10 | 7 | $H_3PO_4$ $H_2O$ $(EtO)_4 Si$ Al—tri-S—B | A | 350 | 1.0 | 100 | 56.9 | 97.8 | 41.8 | 98.7 |
| 11 | 8 | $Ge(OEt)_4$ $H_3PO_4$ $H_2O$ $(EtO)_4 Si$ Al—tri-S—B | A | 350 | 1.0 | 100 | 51.0 | N/D | N/D | N/D |
| 12 | 9 | $Ti(OBu)_4$ Al—tri-S—B $H_3PO_4$ $H_2O$ $(EtO)_4 Si$ Al—tri-S—B | A | 350 | 1.0 | 100 | 72.4 | 94.4 | 23.3 | 95.7 |
| 13 | 10 | $H_3PO_4$ $H_2O$ $(EtO)_4 Si$ Al—tri-S—B | B | 350 | 1.0 | 100 | 62.2 | 81.1 | 23.3 | 85.5 |
| 26 | 13 | $H_3PO_4$ $H_2O$ $(EtO)_4 Si$ Al—tri-S—B | A | 320 | 1.0 | 100 | 75.7 | 84.3 | 11 | 86.7 |
| 27 | 13 | $H_3PO_4$ $H_2O$ $(EtO)_4 Si$ Al—tri-S—B | A | 310 | 1.0 | 100 | 74.6 | 91.2 | 18.2 | 92.8 |
| 28 | 13 | $H_3PO_4$ $H_2O$ $(EtO)_4 Si$ Al—tri-S—B $H_3PO_4$ $H_2O$ | A | 310 | 2.0 | 100 | 70.1 | 99.0 | 29.2 | 99.3 |

$(EtO)_4 Si$ = tetraethyl orthosilicate
Al—tri-S—B = aluminum tri-sec-butoxide
$Ge(OEt)_4$ = germanium tetraethoxide
$Ti(OBu)_4$ = titanium tetrabutoxide
A = a mixture of 10% methylal and 90% methyl propionate, by weight, based on the weight of the mixture
B = a mixture of 10% methylal and 90% propionic acid, by weight, based on the weight of the mixture
N/D = not determined
MMA = methyl methacrylate
MA = methacrylic acid
F = formaldehyde

TABLE 2

| Run No. | Corresponding Comp. Ex. No. | Catalyst Forming Reactants | CATALYST TESTING CONDITIONS |||| Methylal Conversion (%) | Yield of MMA + MA (%) | Selectivity of MMA + MA (%) | Selectivity of F (%) | Yield of MMA + MA + F (%) |
|---|---|---|---|---|---|---|---|---|---|---|
| | | | Reactant Feed Stream | Furnace Temp. (°C.) | Feed Rate (LHSV) | | | | | |
| 14 | 1 | $TiO_2$ $AlPO_4$ $H_3BO_3$ Urea | A | 350 | 1.0 | 91.8 | 16.7 | N/D | N/D | N/D |
| 15 | 1 | $TiO_2$ $AlPO_4$ | A | 370 | 1.0 | 99.1 | 21.3 | N/D | N/D | N/D |

TABLE 2-continued

| Run No. | Corresponding Comp. Ex. No. | Catalyst Forming Reactants | CATALYST TESTING CONDITIONS | | | Methylal Conversion (%) | Yield of MMA + MA (%) | Selectivity of MMA + MA (%) | Selectivity of F (%) | Yield of MMA + MA + F (%) |
|---|---|---|---|---|---|---|---|---|---|---|
| | | | Reactant Feed Stream | Furnace Temp. (°C.) | Feed Rate (LHSV) | | | | | |
| 16 | 1 | $H_3BO_3$ Urea $TiO_2$ $AlPO_4$ | A | 390 | 1.0 | 100 | 20.8 | 66.0 | 68.5 | 89.3 |
| 17 | 2 | $H_3BO_3$ Urea $AlPO_4$ LiOH | A | 350 | 1.0 | 80.1 | 41.1 | 79.2 | 30.9 | 72.0 |
| 18 | 2 | $AlPO_4$ LiOH | A | 370 | 1.0 | 85.0 | 39.0 | 75.7 | 34.8 | 73.8 |
| 19 | 3 | Silica gel impregnated with KOH | A | 370 | 1.0 | 3.4 | 0 | 0 | 3.4 | 3.4 |
| 20 | 3 | Silica gel impregnated with KOH | A | 420 | 1.0 | 3.7 | 0 | 0 | 3.7 | 3.7 |
| 21 | 4 | Silica gel impregnated with Tungstic acid | A | 350 | 1.0 | 51.7 | 4.2 | N/D | N/D | N/D |
| 22 | 5 | Al—tri-S—B $H_3PO_4$ $H_2O$ | A | 350 | 1.0 | 99.6 | 11.1 | N/D | N/D | N/D |
| 23 | 6 | $Ti(OBu)_4$ Al—tri-S—B Boric Acid $H_3PO_4$ $H_2O$ | A | 350 | 1.0 | 100 | 35.8 | N/D | N/D | N/D |
| 24 | 7 | $Si(O_2CCH_3)_4$ Al—tri-S—B $H_3PO_4$ $H_2O$ | A | 350 | 1.0 | 97.4 | 15.5 | N/D | N/D | N/D |
| 25 | 7 | $Si(O_2CCH_3)_4$ Al—tri-S—B $H_3PO_4$ $H_2O$ | A | 350 | 1.0 | 90.3 | 7.2 | N/D | N/D | N/D |

*See Table 1 for abbreviations

DISCUSSION OF RESULTS

Referring to Table 1, it can be seen that all of the methylal conversions of Runs 1 to 12 and 26 to 28 employing methyl propionate as a co-reactant in addition to methylal are 100% at yields of MA+MMA of from 51 to 75.7%. Such yields are achieved with the formation of formaldehyde as the predominant and re-usable by-product such that the yield of MA+MMA+Formaldehye ranges typically from 86.7 to 99.4%. The total conversion of methylal simplifies the re-cycle of by-products since only one by-product, formaldehyde, need be recycled. The high combined selectivities to MA+MMA+F illustrate that the Cannizzaro reaction, which decomposes formaldehyde to $H_2$ and $CO_2$ is substantially if not completely avoided. Similarly, this data show that formaldehyde decomposition which occurs over many metal oxide catalysts as described by Albanesi et al also is substantially avoided. The reduced performance of the catalyst of Run 11 relative to the remainder of Runs 1 to 12 is believed to be attributable to dilution of the amount of Hydrocarboxides I and II in the final catalyst. The titanium diluted catalyst nevertheless performs better than the catalysts of the Comparative Examples particularly in terms of conversion. While Run 13 illustrates a slightly lower combined yield when replacing propionic acid for methyl propionate of MA+MMA+F of 85.5%, the selectivity of MA+MMA is still 81.1%, the yield of MMA+MA is 62.2%, and the methylal conversion is 100%.

The results of Part A of Example 12 illustrate that decarboxylation of methyl propionate and/or propionic acid did not occur when employing the catalyst of the present invention.

Referring to Table 2, Comparative Example 1 illustrates the performance of a $TiO_2$, $AlPO_4$, $H_3BO_3$, urea derived acidic catalyst prepared in general accordance with Example 4 of U.S. Pat. No. 4,118,588. However, contrary to the testing procedure of '588 Example 4 (reaction time 30 min.), in Comparative Example 1, the initial 15 minutes of product are discarded and the product collected thereafter for 2.5 hours was tested. The total methylal conversion was only 91.8% at 350° C. furnace temperature and the yield of MA+MMA was only 16.7%. This contrasts with a reported 95% yield in Example 4 after immediate analysis of product from start-up of the '558 patent. While conversions are improved in Runs 15 and 16 of Comparative Example 1 at higher furnace temperatures of 370° and 390° C., MA+MMA yields still remain drastically below those of the present invention at about 20%.

Comparative Example 2 illustrates the performance of another catalyst disclosed in the '588 patent, namely, LiOH impregnated $AlPO_4$, i.e., methylal conversions of 80 to 85% at MMA+MA yields of about 40%. Such conversions and yields are substantially inferior to those of the present invention.

Comparative Example 3 illustrates an almost non-existent methylal conversion (3.4%) from a conventional basic catalyst, i.e., a KOH silica impregnated gel.

The tungstic acid impregnated silica gel of Comparative Example 4 also performs poorly, producing a methylal conversion of only 51.7% and a MA+MMA yield of 4.2%.

The omission of silicon alkoxide from the catalyst of Comparative Example 5 is believed to be responsible for the substantial drop in MA+MMA yield to 11.1%. It is therefore concluded that Hydrocarboxide II is critical to the performance of the catalyst of the present invention.

Comparative Example 6 further confirms the criticality of Hydrocarboxide II by substituting titanium tetrabutoxide for tetraethyl orthosilicate, and using a boron containing additive. While methylal conversion is 100%, MA+MMA yield is only 35.8%.

Comparative Example 7 illustrates the criticality to the present invention of employing a hydrocarboxide such as an alkoxide in the catalyst preparative procedure, instead of carbonyloxy containing organic moiety such as silicon tetraethyl acetate. Use of the acetate starting material in catalyst preparative method produces a MMA+MA yield of 15.5% (Sample A) and 7.2% (Sample B). These inferior results are believed to be attributable to the formation of acetic acid upon hydrolysis and reaction of the silicon tetraethyl acetate with the acidic phosphorus-oxygen compound. The acetic acid coordinates more strongly with the reaction mixture species and is therefore believed to displace the acetone in the complexes necessary to produce the catalysts of the present invention. Furthermore, it will be noted that Sample A (calcined at 560° C.) performs better than Sample B (calcined at 750° C.). In contrast, the performance of the catalysts of the present invention improve with increasingly higher calcination temperatures above 560° C.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a catalyst composition which comprises:
   (1) reacting in admixture at least one Metal Hydrocarboxide I, at least one Metal Hydrocarboxide II, at least one acidic phosphorus-oxygen containing compound, and water in the presence of at least one liquid organic medium comprising at least 50% by weight, based on the weight of said medium, of at least one member selected from the group consisting of organic aldehyde, organic ketone, and organic ether, said reaction being conducted in a manner sufficient to (a) avoid contact of Metal Hydrocarboxides I and II with water prior to contact of Metal Hydrocarboxide I and II with the acidic phosphorus-oxygen containing compound, and (b) form a catalyst precursor composition;
   (2) separating said catalyst precursor composition from said reaction admixture;
   (3) calcining said catalyst precursor composition to form said catalyst composition;
wherein said process:
   (i) the metal $M^1$, of said Metal Hydrocarboxide I is selected from at least one member of the group consisting of Al, Ga, In, and Tl; and
   (ii) the metal, $M^2$, of said Metal Hydrocarboxide II is selected from at least one member of the group consisting of Si, Sn, and Ge.

2. The process of claim 1 wherein Metal Hydrocarboxide I is represented by the structural formula:

$$(M^1)(OR)_3 \quad (I)$$

wherein $M^1$ is as described in claim 1, and R is at least one substituted or unsubstituted hydrocarbyl radical independently selected from the group consisting of alkyl, aryl, aralkyl, alkaryl, and cycloalkyl, said substituents when present on R being selected from the group consisting of ether groups, ester groups, and mixtures thereof; and Metal Hydrocarboxide II is represented by the structural formula:

$$(M^2)(OR)_4 \quad (II)$$

wherein $M^2$ is as described in claim 1 and R is independently described in conjunction with structural formula I of claim 2.

3. The process of claim 1 wherein the liquid organic medium comprises at least 75%, by weight, based on the weight of said organic medium of at least one aldehyde.

4. The process of claim 1 wherein the liquid organic medium comprises at least 75%, by weight, based on the weight of said organic medium of at least one ketone.

5. The process of claim 1 wherein the liquid organic medium comprises at least 75%, by weight, based on the weight of said organic medium of at least one ether.

6. The process of claim 1 wherein the liquid organic medium is selected from the group consisting of acetone, diethylether, acetaldehyde, methylethyl ketone, 3-pentanone, 1,2-dimethoxyethane and mixtures thereof.

7. The process of claim 1 wherein $M^1$ of Metal Hydrocarboxide I is Al and the $M^2$ of Metal Hydrocarboxide II is Si.

8. The process of claim 7 wherein said Metal Hydrocarboxide I is at least one aluminum alkoxide, and said Metal Hydrocarboxide II is at least one silicon alkoxide.

9. The process of claim 1 wherein said acidic phosphorus-oxygen compound is selected from the group consisting of phosphorus acid, phosphonous acid, phosphinous acid, phosphenous acid, phosphoric acid, phosphonic acid, phosphinic acid, phosphenic acid, phosphine oxide, phosphoranoic acid, phosphorane dioic acid, phosphorane trioic acid, phosphoranetetroic acid, phoshorane pentoic acid, polyphosphoric acid, and mixtures thereof.

10. The process of claim 9 wherein at least one but not all of the acidic hydrogens of said acidic phosphorus-oxygen compounds are replaced with a $C_1$ to $C_{10}$ alkoxide group.

11. The process of claim 9 wherein the acidic phosphorus-oxygen compound is phosphoric acid.

12. The process of claim 1 wherein said catalyst precursor composition is calcined within a temperature range of from about 600° to about 1300° C.

13. The process of claim 12 wherein the calcination temperature is from about 650° to about 1000° C.

14. The process of claim 12 wherein the calcination temperature is from about 700° to about 950° C.

15. The process of claim 12 wherein said catalyst precursor composition is precalcined at a temperature of from about 400° to about 599° C. prior to calcination.

16. The process of claim 1 wherein boron, is incorporated into said catalyst composition.

17. The process of claim 16 wherein boron is incorporated into said catalyst composition by admixing a boron containing compound with said reaction admixture.

18. The process of claim 17 wherein said boron compound is boric acid.

19. The process of claim 1 wherein not greater than 25%, by weight, water based on the combined weight of water and liquid organic medium is present in said reaction admixture.

20. The process of claim 8 which comprises:
(1) providing a liquid reaction admixture comprising:
  (a) Metal Hydrocarboxide I, Metal Hydrocarboxide II, and the acidic phosphorus-oxygen containing compound at respective mole ratios of from about 1:3.5:1.5 to about 1:0.5:0.5;
  (b) water in an amount (i) sufficient to achieve a mole ratio of the sum of the moles of Metal Hydrocarboxides I and II:$H_2O$ of from about 3:1 to about 1:300, and (ii) not greater than about 20%, by weight, based on the weight of liquid organic medium and water in the reaction admixture; and
  (c) liquid organic medium in an amount of at least about 25%, by weight, based on the weight of said liquid admixture, said liquid organic medium being selected to dissolve therein Hydrocarboxides I and II, and the acidic phosphorus-oxygen compound;
(2) providing said liquid admixture at a temperature of from about 5° to about 200° C., for a period of from about 0.15 to about 40 hours in a manner sufficient to achieve intimate contact and reaction between the Metal Hydrocarboxides I and II, water, and the acidic phosphorus-oxygen composition to form a catalyst precursor composition;
(3) separating said catalyst precursor composition from the liquid reaction admixture thereby removing residual organic medium from the catalyst precursor composition and recovering the catalyst precursor as a dry solid material; and
(4) calcining said catalyst precursor composition solid in air within the temperature range of from about 650° to about 1000° C. for a period of from about 1 to about 48 hours to form said catalyst composition.

21. The process of claim 20 wherein:
(a) Metal Hydrocarboxide I, Metal Hydrocarboxide II, and the acidic phosphorus-oxygen composition are present in said admixture at respective mole ratios of from about 1:2:1.25 to about 1:0.7:0.7;
(b) water is present in said reaction admixture in an amount (i) sufficient to achieve a mole ratio of the sum of the moles of Metal Hydrocarboxides I and II:$H_2O$ of from about 2:1 to about 1:10 and (ii) not greater than about 15%, by weight, based on the weight of the liquid organic medium and water;
(c) the liquid organic medium present in said reaction admixture comprises at least 75%, by weight, thereof of any of said aldehyde, ketone, and ether, and said liquid organic medium comprises at least 40%, by weight of said reaction admixture based on the weight of Hydrocarboxides I and II, the acidic phosphorus oxygen composition, liquid organic medium and water;
(d) the catalyst precursor is calcined within a temperature range of from about 700° to about 950° C.

22. The process of claim 20 wherein the liquid organic medium as initially added to said admixture consists essentially of said aldehyde, ketone, ether or mixtures thereof.

23. The process of claim 20 wherein said catalyst precursor composition, prior to separation from the liquid reaction admixture, is aged at a temperature of from about 10° to about 100° C. for a period of from about 1 to about 30 hours.

24. The process of claim 20 wherein the catalyst precursor solids are precalcined at a temperature of from about 400° to about 599° C. for a period of from about 0.1 to about 10 hours prior to calcination thereof.

25. The process of claim 20 wherein said liquid reaction admixture is provided by mixing an anhydrous solution comprising Metal Hydrocarboxides I and II, and liquid organic medium, with a solution comprising the acidic phosphorus-oxygen composition, water, and liquid organic medium.

26. The process of claim 20 wherein the Metal Hydrocarboxide I is selected from the group consisting of aluminum tri-n-butoxide, aluminum tri-sec-butoxide, aluminum tri-isobutoxide, aluminum tri-isopropoxide, aluminum tri-n-propoxide, aluminum tri-ethoxide, and aluminum trimethoxide and mixtures thereof; Metal Hydrocarboxide II is selected from the group consisting of silicon tetraethoxide, silicon tetramethoxide, silicon tetrapropoxide and mixtures thereof; the acidic phosphorus-oxygen compound is phosphoric acid; and the liquid organic medium is selected from the group consisting of acetone, diethylether and mixtures thereof.

27. The process of claim 26 wherein the Metal Hydrocarboxide I is aluminum sec-butoxide and Metal Hydrocarboxide II is silicon tetraethoxide.

* * * * *